United States Patent
Li et al.

(10) Patent No.: US 9,551,639 B2
(45) Date of Patent: Jan. 24, 2017

(54) DEVICE AND METHOD FOR MEASURING TRUE TRIAXIAL CREEP OF GEOTECHNICAL ENGINEERING TEST BLOCK

(71) Applicant: SHANDONG UNIVERSITY, JiNan, ShanDong Province (CN)

(72) Inventors: Shucai Li, JiNan (CN); Liping Li, JiNan (CN); Hongliang Liu, JiNan (CN); Qinghan Wang, JiNan (CN); Shaoshuai Shi, JiNan (CN); Qianqing Zhang, JiNan (CN); Zhenhao Xu, JiNan (CN); Zongqing Zhou, JiNan (CN); Jing Wang, JiNan (CN); Cong Hu, JiNan (CN)

(73) Assignee: SHANDONG UNIVERSITY, Shandong (CN)

( * ) Notice: Subject to any disclaimer, the term of this patent is extended or adjusted under 35 U.S.C. 154(b) by 0 days.

(21) Appl. No.: 14/780,848

(22) PCT Filed: Dec. 2, 2013

(86) PCT No.: PCT/CN2013/001487
§ 371 (c)(1),
(2) Date: Sep. 28, 2015

(87) PCT Pub. No.: WO2014/153697
PCT Pub. Date: Oct. 2, 2014

(65) Prior Publication Data
US 2016/0054211 A1     Feb. 25, 2016

(30) Foreign Application Priority Data

Mar. 27, 2013 (CN) .......................... 2013 1 0103132
Mar. 27, 2013 (CN) ...................... 2013 2 0145784 U

(51) Int. Cl.
*G01N 3/08* (2006.01)

(52) U.S. Cl.
CPC ......... *G01N 3/08* (2013.01); *G01N 2203/0071* (2013.01); *G01N 2203/0256* (2013.01)

(58) Field of Classification Search
CPC .................................... G01N 3/08; G01B 5/30
(Continued)

(56) References Cited

U.S. PATENT DOCUMENTS 7,051,600 B1    5/2006   Cavallaro et al.

FOREIGN PATENT DOCUMENTS

| CN | 102607946   | * | 7/2012 | ............... G01N 3/02 |
| CN | 102607946 A |   | 7/2012 |                            |

(Continued)

OTHER PUBLICATIONS

Mar. 13, 2014 International Search Report issued in International Patent Application No. PCT/CN2013/001487.

(Continued)

*Primary Examiner* — Lisa Caputo
*Assistant Examiner* — Nigel Plumb
(74) *Attorney, Agent, or Firm* — Oliff PLC

(57) ABSTRACT

Device and method for measuring true triaxial creep of a geotechnical engineering test block, including a supporting structure; the device includes four confining pressure-plates and upper-and-lower compression-plates forming an enclosed cavity for the test block; confining pressure-plates include two long confining pressure-plates and two short-confining pressure-plates, upper-and-lower compression-plates are rectangular top and bottom steel-plates, two L-shaped long confining pressure-plates bent towards the outer side lapped on two adjacent side faces of the bottom steel-plate, two L-shaped short-confining pressure-plates bent towards the outer side lapped on remaining two-side faces of the bottom steel-plate, and bottom ends of the short-confining pressure-plates are placed on the bottom (Continued)

steel-plate; top ends of long confining pressure-plates lapped on the top steel-plate, and top steel-plate leans against inner side faces of two short-confining pressure-plates; vertically pressure sensors corresponds to four confining pressure-plates and upper-and-lower compression-plates in the supporting structure, and grating shortrulers on pressure sensors.

8 Claims, 3 Drawing Sheets

(58) Field of Classification Search
 USPC .......................... 73/818, 788, 790, 760, 789
 See application file for complete search history.

(56) References Cited

FOREIGN PATENT DOCUMENTS

| | | | |
|---|---|---|---|
| CN | 103217345 A | 7/2013 | |
| CN | 203164066 U | 8/2013 | |
| JP | 2003-050188 A | 2/2003 | |
| SU | 951103 * | 8/1982 | ............... G01N 3/08 |
| SU | 951103 A1 | 8/1982 | |

OTHER PUBLICATIONS

Mar. 13, 2013 Written Opinion issued in International Patent Application No. PCT/CN2013/001487.

* cited by examiner

DEVICE AND METHOD FOR MEASURING TRUE TRIAXIAL CREEP OF GEOTECHNICAL ENGINEERING TEST BLOCK

FIELD OF THE INVENTION

The present invention relates to a device and a method for measuring true triaxial creep of a geotechnical engineering test block.

BACKGROUND OF THE INVENTION

Creep refers to a phenomenon that the strain of a solid material increases with time extension under the condition of keeping constant stress. The creep is different from plastic deformation, the plastic deformation usually occurs after the stress exceeds an elastic limit, but the creep can occur when the stress is smaller than the elastic limit, as long as the action time of the stress is long enough.

The creep phenomenon is very widespread in geotechnical engineering, and a lot of geotechnical engineering disasters are also closely linked with rock and soil creep, such as landslide, collapse, ground subsidence and the like, thus a study on the creep of rock and soil is very necessary and is an important guarantee for the safety of geotechnical engineering.

Previous geotechnical engineering creep tests tend to stay on uniaxial and false triaxial tests, the influence of a confining pressure of a test block is omitted in the uniaxial test, the inequality of pressures in various directions of the test block is omitted in the false triaxial test, and these cannot accurately reflect the true stress and creep behavior of rock and soil under practical conditions. A true triaxial creep test instrument of rock and soil is very rare at home and abroad, the true triaxial creep test instrument is very complicated in structure, relatively large in scale, complicated in operation and high in cost, can only be used in high-strength creep tests, and often loses accuracy on triaxial creep under low-strength conditions. At present, researches on the creep phenomenon of rock and soil under low-strength conditions are deficient.

SUMMARY OF THE INVENTION

The purpose of the present invention is to overcome the deficiencies of the above prior art and provide a device and a method for measuring true triaxial creep of a geotechnical engineering test block.

To fulfill the above-mentioned purpose, the present invention adopts the following technical solutions:
a device for measuring true triaxial creep of a geotechnical engineering test block includes a supporting structure, wherein the device further includes four confining pressure plates and upper and lower compression plates to form an enclosed cavity for wrapping the test block; the confining pressure plates include two long confining pressure plates and two short confining pressure plates, the upper and lower compression plates are a rectangular top steel plate and a bottom steel plate, two L-shaped long confining pressure plates bent towards the outer side are lapped on two adjacent side faces of the bottom steel plate, two L-shaped short confining pressure plates bent towards the outer side are lapped on the remaining two side faces of the bottom steel plate, and the bottom ends of the short confining pressure plates are placed on the bottom steel plate; the top ends of the long confining pressure plates are lapped on the top steel plate, and the top steel plate leans against the inner side faces of the two short confining pressure plates; pressure sensors are vertically arranged at positions corresponding to the four confining pressure plates and the upper and lower compression plates in the supporting structure, and grating rulers are arranged on the pressure sensors.

The supporting structure includes a bottom plate and a cross top steel bracket, and the four tail ends of the top steel bracket are respectively connected with the bottom plate through lateral steel brackets; hydraulic jacks are respectively arranged at the center of the bottom plate and at the centers of the lateral steel brackets inwards.

The lower end at the crossing site of the top steel bracket is connected with a connecting steel sheet I, the hydraulic jacks are respectively connected with connecting steel sheets II-VI through the pressure sensors, a top pulley is arranged at the lower end of the connecting steel sheet I, a bottom pulley is arranged at the top end of the connecting steel sheet II, and lateral pulleys are arranged on the connecting steel sheets III-VI towards the inner sides; the top pulley supports the top steel plate, the bottom pulley supports the bottom steel plate used for placing a square test block, and the four side faces of the test block are closely jointed with the two long confining pressure plates and the two short confining pressure plates; the lateral pulleys support the outer side faces of the four confining pressure plates.

A confining pressure plate shoulder pulley and a confining pressure plate bottom pulley are respectively arranged on the inner side and the bottom of the shoulder of the confining pressure plate.

A method for measuring true triaxial creep of a geotechnical engineering test block by using the above device specifically includes the following steps:

1) assembling an experimental apparatus, and forming an enclosed cavity to enclose the test block;
2) pre-pressurizing to make the interior of the supporting structure touch the four confining pressure plates and the upper and lower compression plates and maintain stability;
3) adjusting the reading of the pressure sensor corresponding to the bottom steel plate, zero setting the reading, and recording the initial reading of the corresponding grating ruler;
4) respectively adjusting the hydraulic jacks in the x axis direction, the y axis direction and the z axis direction to make the readings of the pressure sensors in the three directions reach a set value respectively and maintain stability; the range of the set value is 0-5 MPa; and
5) measuring creep displacements in the x direction and the y direction, and setting the ascending distance of the bottom steel plate as the axial creep displacement of the test block.

The specific method of step 1) is as follows: setting up the supporting structure, lapping the bottom steel plate on the bottom in the supporting structure, and lapping the two long confining pressure plates on adjacent side faces of the bottom steel plate; placing the test block on the bottom steel plate and leaning the bottom steel plate against the long confining pressure plates, placing the two short confining pressure plates on the bottom steel plate, and contacting the two short confining pressure plates with the test block; placing the top steel plate on the long confining pressure plates to contact with the side faces of the two short confining pressure plates so as to form the enclosed cavity for enclosing the test block.

The specific method of setting up the supporting structure is as follows: respectively connecting the four tail ends of the cross top steel bracket to the bottom plate through the lateral steel brackets; and mounting the hydraulic jacks at the center of the bottom plate and at the centers of the lateral steel brackets inwards; the lower end at the crossing site of the top steel bracket is connected with the connecting steel sheet I, the hydraulic jacks are respectively connected with the connecting steel sheets II-VI through the pressure sensors, the grating rulers are arranged on the pressure sensors, the top pulley is mounted at the lower end of the connecting steel sheet I, the bottom pulley is mounted at the top end of the connecting steel sheet II, and the lateral pulleys are mounted on the connecting steel sheets III-VI towards the inner sides; the top pulley supports the top steel plate, the bottom pulley supports the bottom steel plate, and the lateral pulleys support the outer side faces of the four confining pressure plates.

In step 5), the specific method for measuring the creep displacements in the x direction and the y direction is as follows: measuring once every 30 minutes within one day, and measuring once every 2 hours after the first day.

The working principle of the present invention is as follows:
1. the surrounding of the square test block is wrapped by four groups of surrounding steel plates to approximately simulate the confining pressure by means of the extrusion of the four steel plates;
2. the four groups of steel plates are lapped in a windmill manner, so that relative positions can be freely changed within a certain range in the case of lateral stress;
3. ball pulleys are arranged between the contact surfaces of the four groups of steel plates to reduce the friction resistance and overcome the bias effect at the same time;
4. two groups of baffles are lapped at the upper and lower sides of the test block in a staggered manner to respectively cover two groups of surrounding steel plates, so as to guarantee the free deformation of the test block in the case of axial stress;
5. the outer sides of the surrounding steel plates are connected with the pressure sensors through the ball pulleys, the lateral stress is applied in a pressurization manner of the hydraulic jacks, and the sensors can accurately control the pressure;
6. the axial pressurization of the device cannot be achieved by gravity loading, the device adopts a manner of extruding the test block from bottom to top to guarantee the stability of the entire device.

In the present invention, the four groups of confining pressure plates are mutually lapped with the upper and lower compression plates in a sliding manner to achieve triaxial loading of the test block. The four groups of confining pressure plates are lapped in the windmill manner, so that relative positions can be freely changed within a certain range in the case of lateral stress, to guarantee the stress independence of the x direction and the y direction; the upper and lower compression plates are lapped with the two groups of lateral steel plates in an up and down staggered manner to guarantee the stress independence of the test block in the z axis direction; the windmill-type surrounding structure can be used for applying unequal confining pressures to the lateral direction of the test block and guaranteeing the free deformation in the lateral direction of the test block to guarantee the independence of lateral pressure.

The ball pulleys are arranged between the contact surfaces of the four groups of confining pressure plates to reduce the friction resistance, and can slide freely and relatively. The four groups of confining pressure plates are designed to L shapes to overcome the bias effect of the confining pressure plates in a movement process. The outer sides of the compression plates form contact connection with the pressure sensors in a pulley manner to guarantee that the axial pressure is along the axle center direction of a test piece and guarantee the independence of the axial pressure at the same time.

The two groups of L-shaped long confining pressure plates and the two groups of L-shaped short confining pressure plates are lapped in an up and down staggered manner to achieve free deformation of the test block in the case of axial stress and guarantee the independence of the axial stress of the test block. The outer sides of the L-shaped steel plates form contact connection with the pressure sensors in the pulley manner to guarantee the device to pressurize along the axle center direction of the test block and guarantee the independence of the axial pressure and the lateral pressure of the test block at the same time. The pressurization is achieved by the hydraulic jacks to ensure a constant pressure. The pressure sensors are used for accurately and constantly controlling the pressure. The grating rulers are used for measuring the triaxial displacement of the test block to greatly improve the test precision.

The present invention overcomes the difficulty in the original true triaxial creep, the windmill-type surrounding structure can be used for applying unequal confining pressures to the lateral direction of the test block and can freely deform, and the ball pulleys are used for reducing the friction between the surrounding steel plates and can freely move within a certain range; the electronic pressure sensors control the hydraulic jacks to accurately and constantly pressurize the rock and soil test block to guarantee the test precision; the axial pressure is pressurized from bottom to top to guarantee the free deformation of the axial direction of the test block and guarantee the stability of the entire device.

The present invention has the following beneficial effects:
1. the present invention solves a lot of inconvenience in the original tests and achieves a simulated test of creep of the test block under low pressure;
2. the pressurization manner of the hydraulic jacks is simple and easy to achieve and is convenient to adjust;
3. the deformation in the creep process is slower, the test period is long, and the automatic adjustment and control type pressurization manner of the hydraulic jacks is used for guaranteeing the test precision, which is sufficient enough to meet the demand of a low-strength creep test;
4. the pressure sensors are installed to guarantee a constant creep confining pressure and ensure the accuracy of the low-strength true triaxial creep test;
5. the test block is extruded from bottom to top to guarantee the stability of the entire device;
6. the grating rulers are used for measuring the displacement of the test block to improve the test precision.

DETAILED DESCRIPTION OF THE EMBODIMENTS

Figure 1:
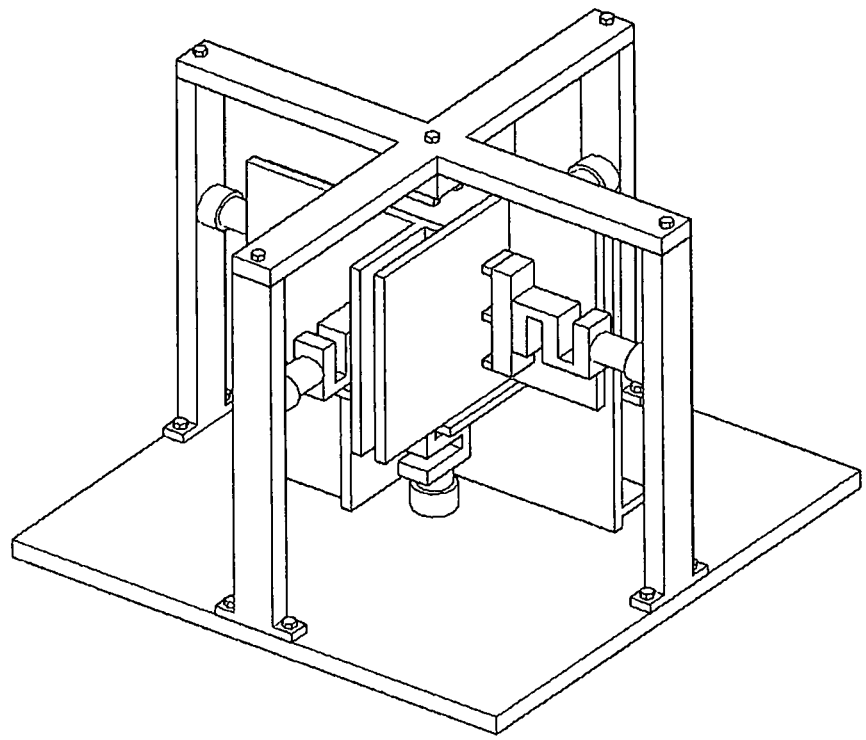
FIG. 1 is a schematic diagram of a structure of the present invention.
Figure 2:
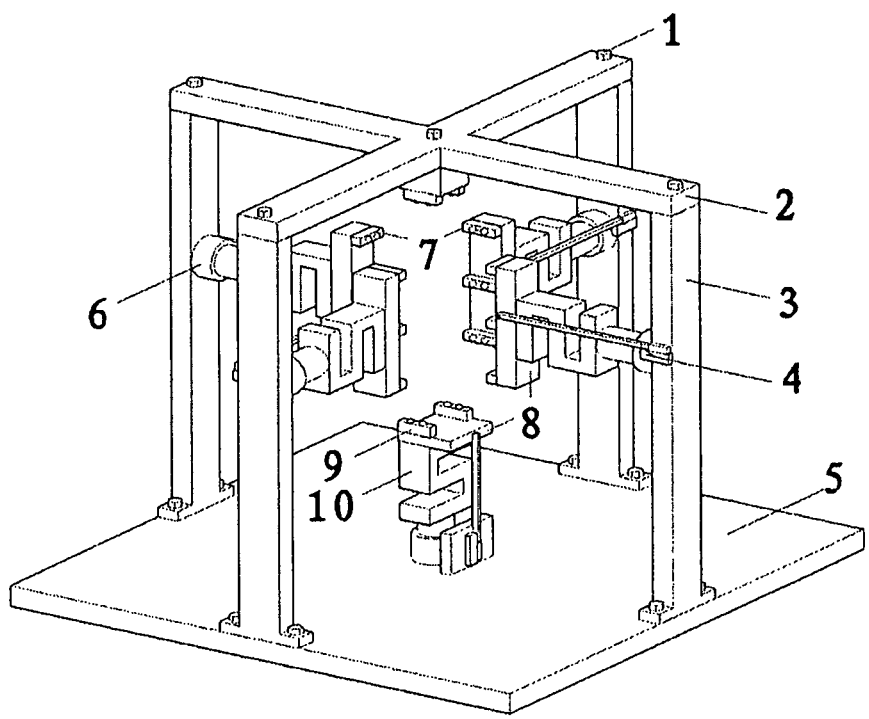
FIG. 2 is a schematic diagram of a structure of a supporting structure.
Figure 3:
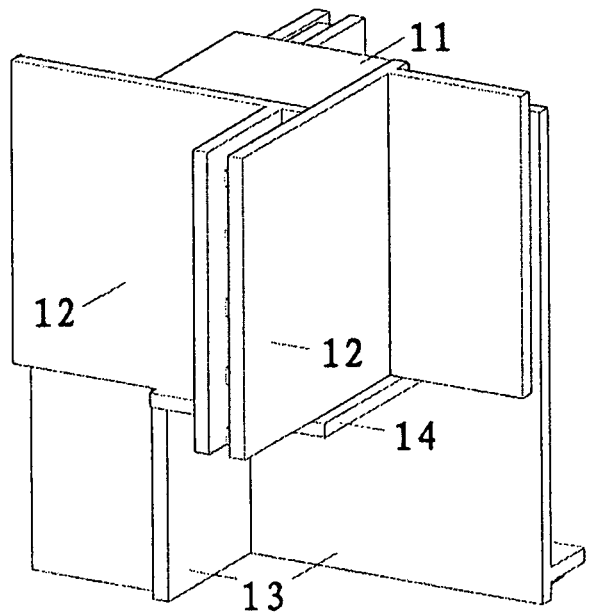
FIG. 3 is a side view in a short confining pressure plate direction.
Figure 4:
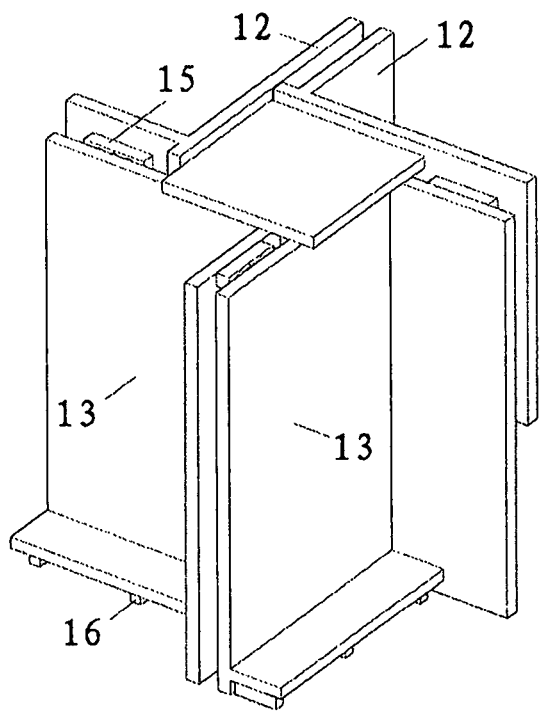
FIG. 4 is a side view in a long confining pressure plate direction.
Figure 5:
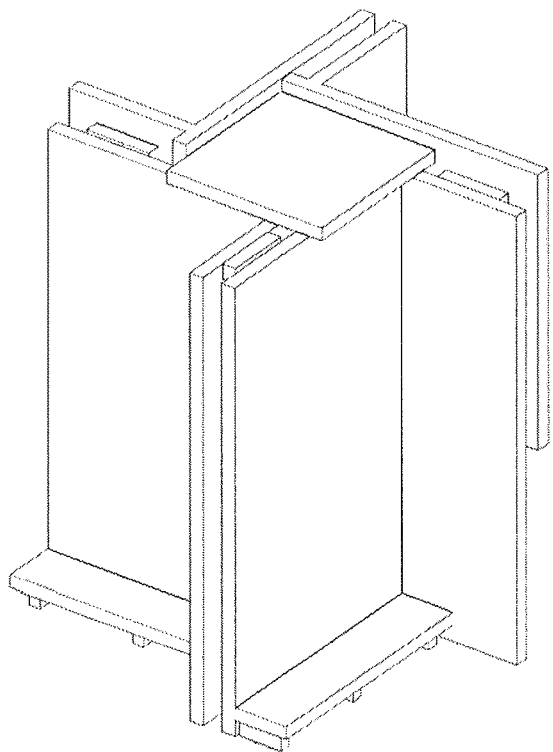
FIG. 5 is a view before loading a test block.
Figure 6:
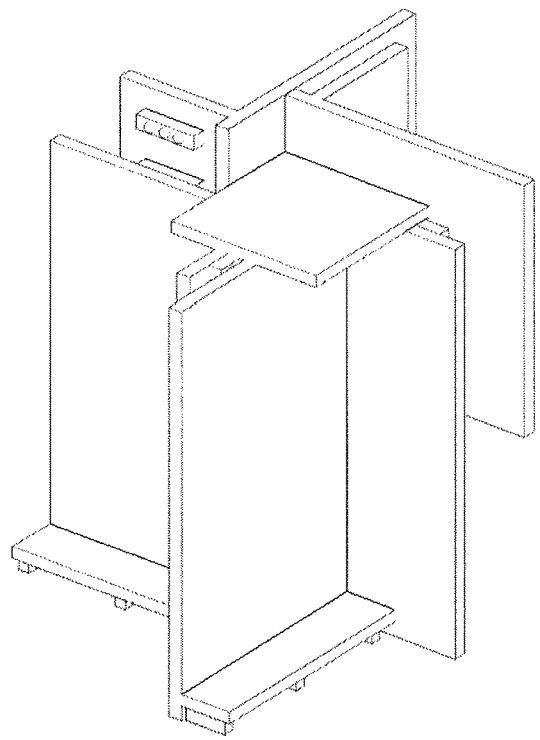
FIG. 6 is a view after loading the test block;
wherein 1 represents a fixing screw, 2 represents a top steel bracket, 3 represents a lateral steel bracket, 4 represents a grating ruler, 5 represents a bottom plate, 6 represents a hydraulic jack, 7 represents a lateral pulley, 8 represents a connecting steel sheet II, 9 represents a bottom pulley, 10 represents a pressure sensor, 11 represents a top steel plate, 12 represents a short confining pressure plate, 13 represents a long confining pressure plate, 14 represents a bottom steel plate, 15 represents a confining pressure plate shoulder pulley and 16 represents a confining pressure plate bottom pulley.

A further illustration of the present invention will be given below in combination with the accompanying drawings and embodiments, but it should be noted that the following descriptions are merely used for explaining the present invention, rather than limiting the contents thereof.

The device provided by the present invention includes a supporting structure, four confining pressure plates and upper and lower compression plates are lapped in the supporting structure in a sliding manner to form an enclosed cavity for enclosing a test block; the confining pressure plates include two long confining pressure plates 13 and two short confining pressure plates 14, the upper and lower compression plates are a rectangular top steel plate 11 and a bottom steel plate 14, two L-shaped long confining pressure plates 13 bent towards the outer side are lapped on two adjacent side faces of the bottom steel plate 14, two L-shaped short confining pressure plates 12 bent towards the outer side are lapped on the remaining two side faces of the bottom steel plate, and the bottom ends of the short confining pressure plates 12 are placed on the bottom steel plate 14; the top ends of the long confining pressure plates 13 are lapped on the top steel plate 11, and the top steel plate 11 leans against the inner side faces of the two short confining pressure plates 12; pressure sensors 10 are vertically arranged at positions corresponding to the four confining pressure plates and the upper and lower compression plates in the supporting structure, and grating rulers 4 are arranged on the pressure sensors 10.

The supporting structure includes a bottom plate 5 and a cross top steel bracket 2, the four tail ends of the top steel bracket 2 are respectively connected with the bottom plate 5 through lateral steel brackets 3, and the connecting sites are fixedly connected by fixing screws 1; hydraulic jacks 6 are respectively arranged at the center of the bottom plate 5 and at the centers of the lateral steel brackets 3 inwards.

The lower end at the crossing site of the top steel bracket 2 is connected with a connecting steel sheet I, the hydraulic jacks 6 are respectively connected with a connecting steel sheet II 8, a connecting steel sheet III, a connecting steel sheet IV, a connecting steel sheet V and a connecting steel sheet VI through the pressure sensors 10, a top pulley is arranged at the lower end of the connecting steel sheet I, a bottom pulley 9 is arranged at the top end of the connecting steel sheet II 8, and lateral pulleys 7 are arranged on the connecting steel sheets III-VI towards the inner sides; the top pulley supports the top steel plate 11, the bottom pulley 9 supports the bottom steel plate 14 used for placing a square test block, and the four side faces of the test block are closely jointed with the two long confining pressure plates 13 and the two short confining pressure plates 12; the lateral pulleys 7 support the outer side faces of the four confining pressure plates.

A confining pressure plate shoulder pulley 15 and a confining pressure plate bottom pulley 16 are respectively arranged on the inner side and the bottom of the shoulder of the confining pressure plate.

A method for measuring true triaxial creep of a geotechnical engineering test block by using the above device specifically includes the following steps:

1) assembling an experimental apparatus, and forming an enclosed cavity to enclose the test block;
2) pre-pressurizing to make the interior of the supporting structure touch the four confining pressure plates and the upper and lower compression plates and maintain stability;
3) adjusting the reading of the pressure sensor 10 corresponding to the bottom steel plate 14, zero setting the reading, and recording the initial reading of the corresponding grating ruler 4;
4) respectively adjusting the hydraulic jacks 6 in the x axis direction, the y axis direction and the z axis direction to make the readings of the pressure sensors 10 in the three directions reach a set value respectively and maintain stability; the range of the set value is 0-5 MPa; and
5) measuring creep displacements in the x direction and the y direction, and setting the ascending distance of the bottom steel plate 14 as the axial creep displacement of the test block.

The specific method of step 1) is as follows: setting up the supporting structure, lapping the bottom steel plate 14 on the bottom in the supporting structure, and lapping the two long confining pressure plates 13 on adjacent side faces of the bottom steel plate 14; placing the test block on the bottom steel plate 14 and leaning the bottom steel plate against the long confining pressure plates 13, placing the two short confining pressure plates 12 on the bottom steel plate 14, and contacting the two short confining pressure plates with the test block; placing the top steel plate 11 on the long confining pressure plates 13 to contact with the side faces of the two short confining pressure plates 12 so as to form the enclosed cavity for enclosing the test block.

The specific method of setting up the supporting structure is as follows: respectively connecting the four tail ends of the cross top steel bracket 2 to the bottom plate through the lateral steel brackets 3; and mounting the hydraulic jacks 6 at the center of the bottom plate 5 and at the centers of the lateral steel brackets 3 inwards; the lower end at the crossing site of the top steel bracket 2 is connected with the connecting steel sheet I, the hydraulic jacks 6 are respectively connected with the connecting steel sheet II 8, the connecting steel sheet III, the connecting steel sheet IV, the connecting steel sheet V and the connecting steel sheet VI through the pressure sensors 10, the grating rulers 4 are arranged on the pressure sensors 10, the top pulley is mounted at the lower end of the connecting steel sheet I, the bottom pulley 9 is mounted at the top end of the connecting steel sheet II 8, and the lateral pulleys 7 are mounted on the connecting steel sheets III-VI towards the inner sides; the top pulley supports the top steel plate, the bottom pulley 9 supports the bottom steel plate 14, and the lateral pulleys 7 support the outer side faces of the four confining pressure plates.

In step 5), the specific method for measuring the creep displacements in the x direction and the y direction is as follows: measuring once every 30 minutes within one day, and measuring once every 2 hours after the first day.

Although the embodiments of the present invention have been described above in combination with the accompanying drawings, the protection scope of the present invention is not limited hereto, based on the technical solutions of the present invention, those skilled in the art can make a variety of modifications or deformations without any creative effort, and these modifications or deformations shall still fall within the protection scope of the present invention.

The invention claimed is:

1. A device for measuring true triaxial creep of a geotechnical engineering test block, comprising a supporting structure, wherein the device further comprises:
   four confining pressure plates and upper and lower compression plates so as to form an enclosed cavity for enclosing the test block;
   wherein the upper and lower compression plates are a rectangular top steel plate and a bottom steel plate,
   wherein the four confining pressure plates include two long confining pressure plates that are L-shaped, are bent towards the outer side and are lapped on two adjacent side faces of the bottom steel plate,
   wherein the four confining pressure plates include two short confining pressure plates that are L-shaped, are bent towards the outer side and are lapped on the remaining two side faces of the bottom steel plate,
   wherein bottom ends of the short confining pressure plates are placed on the bottom steel plate, top ends of the long confining pressure plates are lapped on the top steel plate, and the top steel plate leans against the inner side faces of the two short confining pressure plates,
   wherein pressure sensors are vertically arranged at positions corresponding to the four confining pressure plates and the upper and lower compression plates in the supporting structure, and grating rulers are arranged on the pressure sensors, and
   wherein the two short confining pressure plates and the two long confining pressure plates each have a first portion and a second portion, the first and second portion together defining the L-shape, and a meeting point of the first and second portion for at least one of the long confining pressure plates is toward a geometric center of the supporting structure and disposed under the top steel plate so as to be covered by the top steel plate.

2. The device of claim 1, wherein the supporting structure comprises a bottom plate and a cross top steel bracket, and the four tail ends of the top steel bracket are respectively connected with the bottom plate through lateral steel brackets; hydraulic jacks are respectively arranged at the center of the bottom plate and at the centers of the lateral steel brackets inwards.

3. The device of claim 2, wherein the lower end at the crossing site of the top steel bracket is connected with a connecting steel sheet I, the hydraulic jacks are respectively connected with connecting steel sheets II-VI through the pressure sensors, a top pulley is arranged at the lower end of the connecting steel sheet I, a bottom pulley is arranged at the top end of the connecting steel sheet II, and lateral pulleys are arranged on the connecting steel sheets III-VI towards the inner sides; the top pulley supports the top steel plate, the bottom pulley supports the bottom steel plate used for placing a square test block, and the four side faces of the test block are closely jointed with the two long confining pressure plates and the two short confining pressure plates; the lateral pulleys support the outer side faces of the four confining pressure plates.

4. The device of claim 1, wherein a confining pressure plate shoulder pulley and a confining pressure plate bottom pulley are respectively arranged on the inner side and the bottom of the shoulder of the confining pressure plate.

5. A method for measuring true triaxial creep of a geotechnical engineering test block by using the device of claim 1, specifically comprising the following steps:
   1) assembling an experimental apparatus, and forming an enclosed cavity to enclose the test block;
   2) pre-pressurizing to make the interior of the supporting structure touch the four confining pressure plates and the upper and lower compression plates and maintain stability;
   3) adjusting the reading of the pressure sensor corresponding to the bottom steel plate, zero setting the reading, and recording the initial reading of the corresponding grating ruler;
   4) respectively adjusting the hydraulic jacks 6 in the x axis direction, the y axis direction and the z axis direction to make the readings of the pressure sensors 10 in the three directions reach a set value respectively and maintain stability; the range of the set value is 0-5 MPa; and
   5) measuring creep displacements in the x direction and the y direction, and setting the ascending distance of the bottom steel plate as the axial creep displacement of the test block.

6. The method of claim 5, wherein the specific method of step 1) is as follows: setting up the supporting structure, lapping the bottom steel plate on the bottom in the supporting structure, and lapping the two long confining pressure plates on adjacent side faces of the bottom steel plate; placing the test block on the bottom steel plate and leaning the bottom steel plate against the long confining pressure plates, placing the two short confining pressure plates on the bottom steel plate, and contacting the two short confining pressure plates with the test block; placing the top steel plate on the long confining pressure plates to contact with the side faces of the two short confining pressure plates, so as to form the enclosed cavity for enclosing the test block.

7. The method of claim 6, wherein the specific method of setting up the supporting structure is as follows: respectively connecting the four tail ends of the cross top steel bracket to the bottom plate through the lateral steel brackets; and mounting the hydraulic jacks at the center of the bottom plate and at the centers of the lateral steel brackets inwards; the lower end at the crossing site of the top steel bracket is connected with the connecting steel sheet I, the hydraulic jacks are respectively connected with the connecting steel sheets II-VI through the pressure sensors, the grating rulers are arranged on the pressure sensors, the top pulley is mounted at the lower end of the connecting steel sheet I, the bottom pulley is mounted at the top end of the connecting steel sheet II, and the lateral pulleys are mounted on the connecting steel sheets III-VI towards the inner sides; the top pulley supports the top steel plate, the bottom pulley supports the bottom steel plate, and the lateral pulleys support the outer side faces of the four confining pressure plates.

8. The method of claim 5, wherein in step 5), the specific method for measuring the creep displacements in the x direction and the y direction is as follows: measuring once every 30 minutes within one day, and measuring once every 2 hours after the first day.

* * * * *